United States Patent
Storm

(10) Patent No.: US 8,731,652 B2
(45) Date of Patent: May 20, 2014

(54) METHOD AND APPARATUS FOR MONITORING THE AUTONOMOUS NERVOUS SYSTEM OF A SEDATED PATIENT

(75) Inventor: Hanne Storm, Oslo (NO)

(73) Assignee: Med Storm Innovation AS, Cislo (NO)

(*) Notice: Subject to any disclaimer, the term of this patent is extended or adjusted under 35 U.S.C. 154(b) by 799 days.

(21) Appl. No.: 12/922,689

(22) PCT Filed: Mar. 16, 2009

(86) PCT No.: PCT/NO2009/000099
§ 371 (c)(1),
(2), (4) Date: Feb. 15, 2011

(87) PCT Pub. No.: WO2009/116872
PCT Pub. Date: Sep. 24, 2009

(65) Prior Publication Data
US 2011/0144523 A1 Jun. 16, 2011

(30) Foreign Application Priority Data
Mar. 17, 2008 (NO) .................................... 20081401

(51) Int. Cl.
*A61B 5/053* (2006.01)
(52) U.S. Cl.
USPC ............................. 600/547; 600/306; 600/557
(58) Field of Classification Search
CPC ...................................................... A61B 5/053
USPC .......... 600/300, 301, 306, 547, 548, 554, 557
See application file for complete search history.

(56) References Cited

U.S. PATENT DOCUMENTS

| | | | | |
|---|---|---|---|---|
| 5,897,505 A * | 4/1999 | Feinberg et al. | ............... | 600/547 |
| 6,091,973 A * | 7/2000 | Colla et al. | .................... | 600/324 |
| 7,215,994 B2 * | 5/2007 | Huiku | ............................ | 600/544 |
| 8,439,836 B2 * | 5/2013 | Storm | ............................ | 600/306 |
| 2005/0010257 A1 * | 1/2005 | Lincoln et al. | .................. | 607/14 |
| 2005/0182338 A1 * | 8/2005 | Huiku | ............................ | 600/544 |
| 2007/0276609 A1 | 11/2007 | Greenwald | | |

FOREIGN PATENT DOCUMENTS

| | | |
|---|---|---|
| JP | 9-10312 | 1/1997 |
| JP | 2005-524464 | 8/2005 |
| WO | 03094726 | 11/2003 |
| WO | 2006/083178 | 8/2006 |
| WO | 2006/090371 | 8/2006 |
| WO | 2007/097634 | 8/2007 |

* cited by examiner

*Primary Examiner* — Max Hindenburg
*Assistant Examiner* — John Pani
(74) *Attorney, Agent, or Firm* — Christian D. Abel

(57) ABSTRACT

A method and an apparatus for monitoring the autonomous nervous system of a sedated patient. The method comprises steps of providing a skin conductance signal measured at an area of the patient's skin through a measurement interval, calculating a characteristic of said skin conductance signal, establishing a first output signal indicating the state of pain or discomfort in the patient, and a second output signal indicating the state of awakening in the patient, based on said characteristic of said skin conductance signal. The calculating of the signal characteristic comprises calculating a value representative of a statistical dispersion, e.g., the standard deviation, of the values of the skin conductance signal through the measurement interval.

11 Claims, 2 Drawing Sheets

METHOD AND APPARATUS FOR MONITORING THE AUTONOMOUS NERVOUS SYSTEM OF A SEDATED PATIENT

TECHNICAL FIELD

The invention relates in general to medical technology, and in particular to a method and an apparatus for monitoring a sedated patient.

BACKGROUND OF THE INVENTION

During surgery it is very important to observe the patient's level of consciousness and awareness. Few reliable methods of observation exist today. In the field of medical technology there is a problem in producing physical measurements representing the activity in an individual's autonomous nervous system, i.e. in the part of the nervous system, which is beyond the control of the will.

Particularly, there is a special need to monitor the autonomous nervous system of a sedated, non-verbal patient, e.g. a patient in anaesthesia or an artificially ventilated patient, in order to detect if the patient needs more hypnotics because of awakening stimuli or more analgesia because of pain stimuli.

Tests have shown that the skin's conductance changes as a time variable signal which, in addition to a basal, slowly varying value (the so-called basal level or the average conductance level through a certain interval), also has a component consisting of spontaneous waves or fluctuations.

The basal level and the characteristics of the fluctuations may be viewed on a display by a skilled, human operator (e.g., the surgeon or the anesthesiologist), in order to monitor the autonomous nervous system of the patient.

RELATED BACKGROUND ART

WO-03/94726 discloses a method and an apparatus for monitoring the autonomous nervous system of a sedated patient. In the method, a skin conductance signal is measured at an area of the patient's skin. Certain characteristics, including the average value of the skin conductance signal through a time interval and the number of fluctuation peaks through the interval, is calculated. Based on these characteristics, two output signals are established, indicating pain/discomfort and awakening in the patient, respectively. The awakening signal is established based on the number of fluctuations and the average value through an interval.

SUMMARY OF THE INVENTION

An object of the present invention is to provide an improved method and an improved apparatus for monitoring a sedated patient.

The method and the apparatus are defined by the appended claims.

BRIEF DESCRIPTION OF THE DRAWINGS

The principle of the invention will be disclosed in the following by an example embodiment, illustrated in the figures.

DETAILED DESCRIPTION OF THE INVENTION

Figure 1:
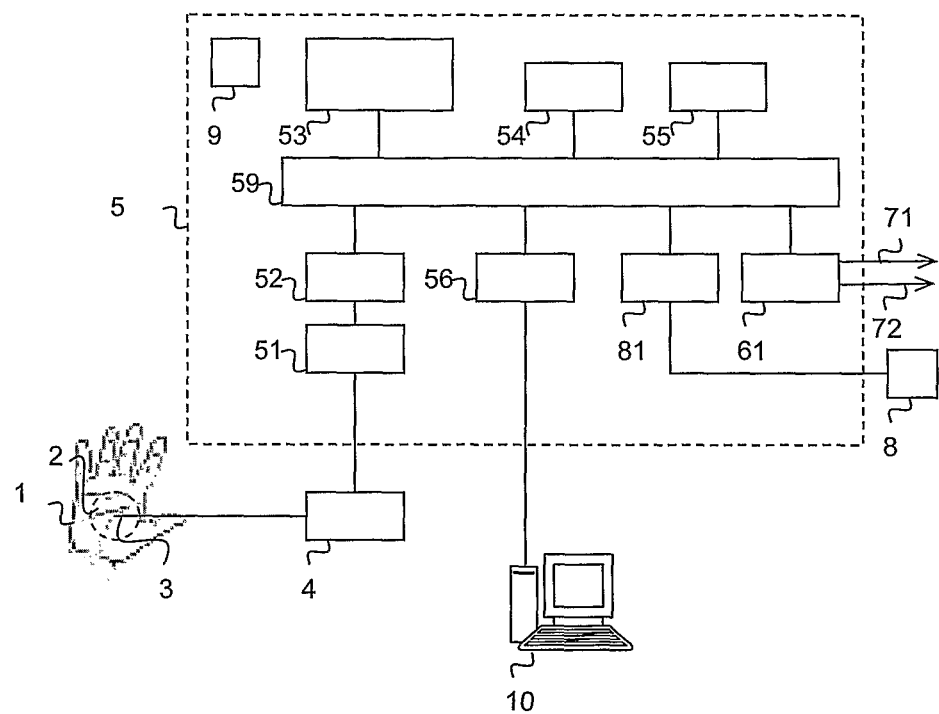
FIG. 1 illustrates a block diagram for a preferred embodiment of an apparatus according to the invention.

FIG. 1 illustrates a block diagram for a preferred embodiment of an apparatus according to the invention.

Substantial parts of the apparatus' hardware structure is previously described in the Applicant's related patent application published as WO-03/94726, with particular reference to the block diagram in the publication's FIG. 1 and the corresponding, detailed description. The disclosure of this publication, and the apparatus hardware structure in particular, is hereby expressly incorporated by reference.

On an area 2 of the skin on a body part 1 of the patient, sensor means 3 are placed for measuring the skin's conductance. The body part 1 is preferably a hand or a foot, and the area 2 of the skin on the body part 1 is preferably the palmar side of the hand or the plantar side of the foot. Alternatively, the body part 1 may be the forehead of the patient. The sensor means 3 comprise contact electrodes where at least two electrodes are placed on the skin area 2. In a preferred embodiment the sensor means 3 consist of three electrodes: a signal electrode, a measuring electrode and a reference voltage electrode, which ensures a constant application of voltage over the stratum corneum (the surface layer of the skin) under the measuring electrode. The measuring electrode and the signal electrode are preferably placed on the skin area 2. The reference voltage electrode may also be placed on the skin area 2, but it is preferably placed in a nearby location, suitable for the measuring arrangement concerned.

In an embodiment, an alternating current is used for measuring the skin's conductance. The alternating current advantageously has a frequency in the range of up to 1000 Hz, such as 88 Hz. A signal generator, operating at the specified frequency, applies a signal current to the signal electrode.

The resulting current through the measuring electrode is conveyed to a measurement converter 4, which includes a current to voltage converter and a decomposition circuit which provides the conductance real part of the complex admittance.

The measurement converter 4 may also comprise amplifier and filter circuits. In the preferred embodiment the measurement converter contains low-pass filters, both at the input and at the output. The object of the input low-pass filter is to attenuate high-frequency noise, for instance coming from other medical equipments, and also to serve as anti-aliasing filter to prevent high frequency components from being received by subsequent circuits for time discretization.

The control unit 5 comprises a time discretization unit 51 for time discretization of the signal from the measurement converter. The time discretization takes place at a sampling rate, which may advantageously be in the order of 20 to 200 samplings per second. The control unit further comprises an analog-digital converter 52, which converts measurement data to digital form.

The control unit 5 also comprises a processing unit 53 for processing the digitized measurement data, storage means in the form of at least one store for storing data and programs, illustrated as a non-volatile memory 54 and a random access memory 55. The control unit 5 further comprises an output interface circuit 61, which provides output signals 71, 72. Preferably, the control unit 5 further comprises a display interface circuit 81, which is further connected to display unit 8. The control unit 5 may also advantageously comprise a communication port 56 for digital communication with an external unit, such as a personal computer 10.

In a preferred embodiment the non-volatile memory 54 comprises a read-only storage in the form of programmable ROM circuits, or alternatively Flash memory circuits, containing at least a program code and permanent data, and the random access memory 55 comprises RAM circuits, for storage of measurement data and other provisional data.

The control unit 5 also comprises an oscillator (not shown), which delivers a clock signal for controlling the processing unit 53. The processing unit 53 also contains timing means (not shown) in order to provide an expression of the current time, for use in the analysis of the measurements. Such timing means are well-known to those skilled in the art, and are often included in micro controllers or processor systems which the skilled person will find suitable for use with the present invention.

The control unit 5 may be realized as a microprocessor-based unit with connected input, output, memory and other peripheral circuits, or it may be realized as a micro controller unit where some or all of the connected circuits are integrated. The time discretization unit 51 and/or analog-digital converter 52 may also be included in such a unit. The choice of a suitable form of control unit 5 involves decisions, which are suitable for a person skilled in the art.

An alternative solution is to realize the control unit as a digital signal processor (DSP).

According to the invention, a novel and inventive method is performed by the control unit 5, in order to analyze the skin conductance signal. By means of the program code, the control unit 5 is particularly arranged to perform the method in accordance with the invention, such as the method exemplified with reference to FIG. 2 below.

The control unit 5 is arranged to read time-discrete and quantized measurements for the skin conductance from the measurement converter 4, preferably by means of an executable program code, which is stored in the non-volatile memory 54 and which is executed by the processing unit 53. It is further arranged to enable measurements to be stored in the read and write memory 55. By means of the program code, the control unit 5 is further arranged to analyze the measurements in real time, i.e. simultaneously or parallel with the performance of the measurements.

In this context, simultaneously or parallel should be understood to mean simultaneously or parallel for practical purposes, viewed in connection with the time constants which are in the nature of the measurements. This means that input, storage and analysis can be undertaken in separate time intervals, but in this case these time intervals, and the time between them, are so short that the individual actions appear to occur concurrently.

The control unit 5 is further arranged to identify the fluctuations in the skin conductance signal. In particular, the control unit 5 is arranged to calculate a value representative of a statistical dispersion, e.g. the standard deviation, of the values of the skin conductance signal through the measurement interval.

Figure 2:
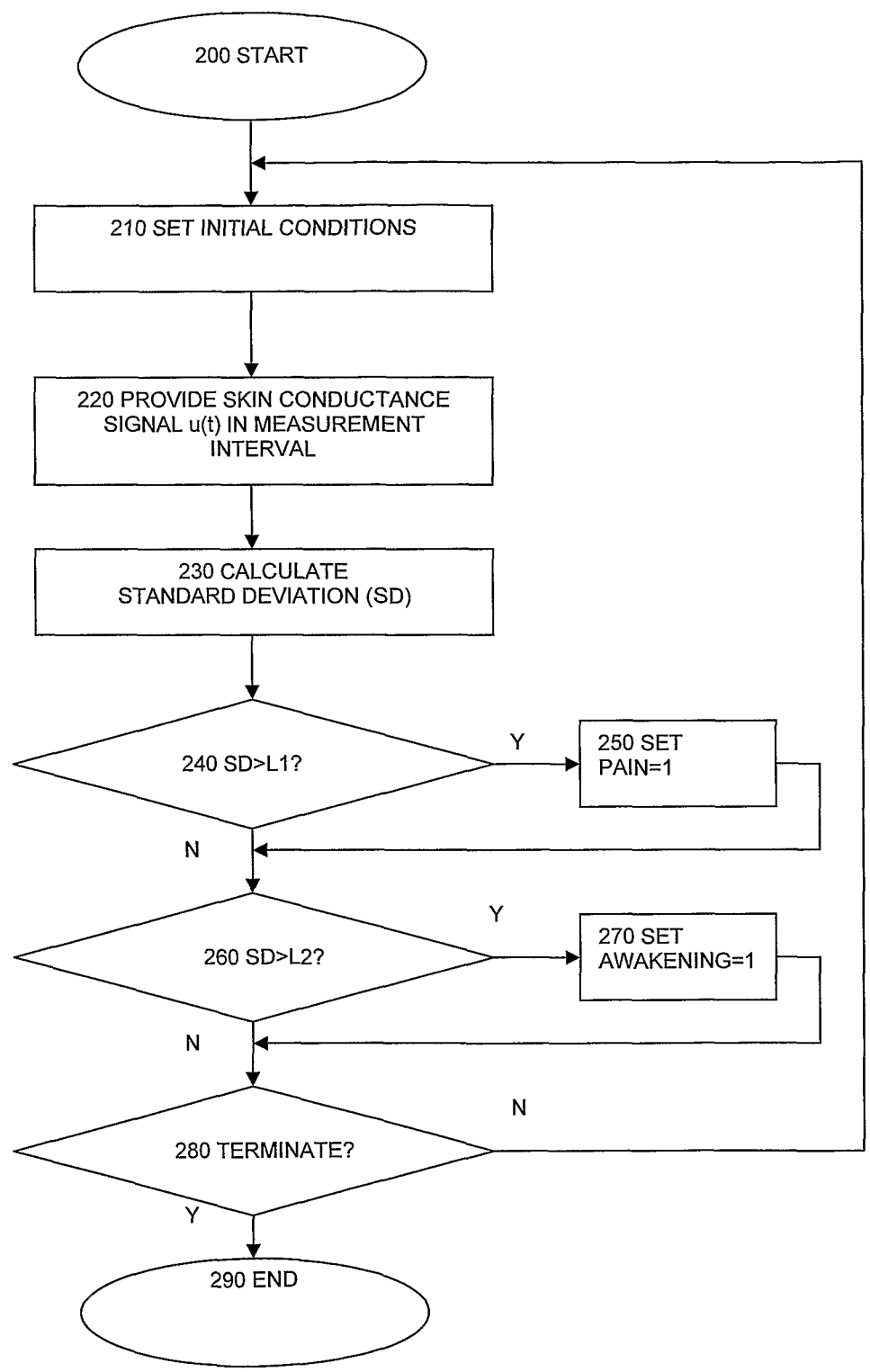
FIG. 2 illustrates a flow chart for a method according to the invention.

Further functions of the control unit are described below with reference to the method illustrated in FIG. 2.

All the above mentioned functions of the control unit 5 may be achieved by appropriate computer program portions included in the memory, preferably the non-volatile memory 54.

The processing unit 53, the memories 54, 55, the analog/digital converter 52, the communication port 56, the interface circuit 81 and the interface circuit 61 are all connected to a bus unit 59. The detailed construction of such bus architecture for the design of a microprocessor-based instrument is regarded as well-known for a person skilled in the art.

The interface circuit 61 is a digital or analog output circuit, which generates a digital or analog representation of first and second output signals 71, 72 from the processing unit 53 via the bus unit 59 when the interface circuit 61 is addressed by the program code executed by the processing unit 53.

The first and second output signals 71, 72 reflects the state of the patient's autonomous nervous system. In particular, the first output signal 71 indicates a state of pain or discomfort in the patient, and the second output signal 72 indicates a state of awakening in the patient. The output signals 71, 72 may conveniently be indicated by appropriate indicators, such as visual and/or audible indicators, in the apparatus.

The apparatus further comprises a power supply unit 9 for supplying operating power to the various parts of the apparatus. The power supply may be a battery or a mains supply.

The apparatus may advantageously be adapted to suit the requirements regarding hospital equipment, which ensures patient safety. Such safety requirements are relatively easy to fulfill if the apparatus is battery-operated. If, on the other hand, the apparatus is mains operated, the power supply shall meet special requirements, or requirements are made regarding a galvanic partition between parts of the apparatus (for example, battery operated), which are safe for the patient and parts of the apparatus, which are unsafe for the patient. If the apparatus has to be connected to external equipment, which is mains operated and unsafe for the patient, the connection between the apparatus, which is safe for the patient and the unsafe external equipment requires to be galvanically separated. Galvanic separation of this kind can advantageously be achieved by means of an optical partition. Safety requirements for equipment close to the patient and solutions for fulfilling such requirements in an apparatus like that in the present invention are well-known to those skilled in the art FIG. 2 illustrates a flow chart of a method according to the invention.

The method is preferably executed by a processing device in an apparatus for providing an output signal that reflects the state of the autonomous nervous system of a sedated patient, e.g. the processing device 53 in the control unit 5 illustrated in FIG. 1.

The method starts at the initial step 200.

Initial conditions are set in step 210. The initial condition setting step 210 may include setting a setting a measurement interval and resetting the first 71 and second 72 output signals, i.e. as indicating no pain and no awakening in the patient.

The measurement interval may e.g. be in the range [5 seconds, 40 seconds] or in the range [10 seconds, 30 seconds] or about 20 seconds. Other intervals are also possible.

Next, in the signal providing step 220, a skin conductance signal u(t) measured at an area of the patient's skin is provided through the measurement interval. The signal may be represented as numeric values stored in a memory, e.g. in the random access memory 55, in the apparatus.

Next, in the characteristics calculating step 230, a characteristic of the skin conductance signal is calculated, e.g. by the processing device 53. The calculating step 230 comprises calculating a value representative of a statistical dispersion of the values of the skin conductance signal through the measurement interval.

In an embodiment the calculating step 230 includes calculating a standard deviation of the values of the skin conductance signal through the measurement interval.

Alternatively, the calculating step 230 may comprise a statistical function selected from the set consisting of: variance, interquartile range, range, mean difference, median absolute deviation, average absolute deviation, coefficient of variation, quartile coefficient of dispersion, relative mean difference, and variance-to-mean ratio.

For explanatory purposes, it will be assumed in the subsequent detailed description that the standard deviation is calculated in step 230. However, the skilled person will readily understand that the remaining method steps, and in particular the establishment of limit values used in those steps, may easily be adapted in case another statistical function is used for calculating the statistical dispersion of the values of the skin conductance in the calculating step 230.

Next, in the first comparison step 240, the value representative of the statistical dispersion of the skin conductance signal, such as the standard deviation, is compared with a first, predetermined limit value L1.

If the statistical dispersion is standard deviation, the first limit value L1 is advantageously in the range [0.01 μS, 0.30 μS]. More preferably, the first limit value L1 may be in the range [0.02 μS, 0.10 μS]. Most preferably the first limit value L1 is about 0.03 μS.

If another statistical function is used for statistical dispersion, corresponding ranges for the first limit value L1 may readily be calculated based on the teachings of the present specification.

If the value representing the statistical dispersion (e.g., the standard deviation) exceeds the first limit value L1, the first output signal setting step 250 is performed. In this step, the first output signal 71 is set as indicating pain or discomfort in the patient. Then the method continues at the second comparison step 260.

If the value representing the statistical dispersion does not exceed the first limit value L1, the method continues directly at the second comparison step 260.

Next, in the second comparison step 260, the value representative of the statistical dispersion of the skin conductance signal, such as the standard deviation, is compared with a second, predetermined limit value L2.

If the statistical dispersion is standard deviation, the second limit value L2 is advantageously in the range [0.06 μS, 18.0 μS]. More preferably, the second limit value L2 may be in the range [0.10 μS, 3.0 μS]. Most preferably the second limit value L2 is about 0.5 μS.

If another statistical function is used for statistical dispersion, corresponding ranges for second limit value L2 may readily be calculated based on the teachings of the present specification.

If the value representing the statistical dispersion (e.g., the standard deviation) exceeds the second limit value L2, the second output signal setting step 270 is performed. In this step, the second output signal 72 is set as indicating awakening in the patient. Subsequent to the second output signal step 270 the method continues at the terminating decision step 280.

If the value representing the statistical dispersion does not exceed the second limit, the method continues directly at the terminating test step 280.

In the terminating test step 280 a test is performed in order to determine if the process shall be terminated. The determination may be based on, e.g., a manual user input. If the method is decided to terminate, the method terminates at step 290. Else, the method is repeated from the initial condition setting step 210.

The above description and drawings present a specific embodiment of the invention. It will be obvious to the skilled person that numerous alternative or equivalent embodiments exist within the scope of the present invention. For instance, the measurement of skin impedance (including skin resistance) instead of skin conductance will lead to equivalent results, provided that the inverse nature of these variables is taken into account in the subsequent processing of the measurement signal.

When the term "patient" is used throughout the specification and claims, is should be appreciated that although the present invention is primarily directed towards the monitoring of human beings, the invention has also been proven to be applicable for monitoring animals, in particular mammals. Consequently, the term "patient" should be interpreted as covering both human and animal patients.

The inventive concept is not limited to the exemplary embodiments described above. Rather, the scope of the invention is set forth in the following patent claims.

The invention claimed is:

1. A method for monitoring the autonomous nervous system of a sedated patient, comprising:
    measuring, by an electrode arrangement and a measurement converter, a skin conductance signal at an area of the patient's skin through a measurement interval,
    calculating, by a processing device, a characteristic of said skin conductance signal,
    establishing, by a processing device, a first output signal indicating a state of pain or discomfort in the patient, based on said characteristic of said skin conductance signal,
    establishing, by a processing device, a second output signal indicating a state of awakening in the patient, based on said characteristic of said skin conductance signal,
    wherein said step of calculating said characteristic comprises
    calculating, by a processing device, a value representative of a statistical dispersion of values of said skin conductance signal through said measurement interval, the value being a standard deviation of the values of said skin conductance signal through said measurement interval,
    further wherein said step of establishing said first output signal indicating the state of pain or discomfort in the patient comprises comparing said standard deviation with a first limit value, the first signal being established as indicating pain or discomfort in the patient if the standard deviation exceeds the first limit value, and wherein said step of establishing said second output signal indicating the state of awakening in the patient comprises comparing said standard deviation with a second limit value, the second signal being established as indicating awakening in the patient if the standard deviation exceeds the second limit value.

2. The method according to claim 1, wherein said first limit value is in the range [0.01 μS, 0.30 μS].

3. The method according to claim 2, wherein said first limit value is in the range [0.02 μS, 0.10 μS].

4. The method according to claim 3, wherein said first limit value is 0.03 μS.

5. The method according to claim 1, wherein said second limit value is in the range [0.06 μS, 18.0 μS].

6. The method according to claim 5, wherein said second limit value is in the range [0.10 μS, 3.0 μS].

7. The method according to claim 6, wherein said second limit value is 0.5 μS.

8. The method according to one of the preceding claims, wherein said measurement interval is in the range [5 seconds, 40 seconds].

9. The method according to claim 8, wherein said measurement interval is in the range [10 seconds, 30 seconds].

10. The method according to claim 9. wherein said measurement interval is 15 seconds.

11. An apparatus for monitoring a sedated patient, comprising
    measurement equipment for providing a skin conductance signal measured at an area of the patient's skin, and
    a control unit, including a processing device which is configured to perform the following steps:

calculating a characteristic of said skin conductance signal,
establishing a first output signal indicating a state of pain or discomfort in the patient, based on said characteristic of said skin conductance signal,
establishing a second output signal indicating a state of awakening in the patient, based on said characteristic of said skin conductance signal,
wherein the processing device is configured to calculate said characteristic by
calculating a value representative of a statistical dispersion of the values of said skin conductance signal through said measurement interval, the value being a standard deviation of values of said skin conductance signal through said measurement interval,
wherein the processing device is configured to establish said first output signal indicating the state of pain or discomfort in the patient by comparing said standard deviation with a first limit value, the first signal being established as indicating pain or discomfort in the patient if the standard deviation exceeds the first limit value, and
wherein the processing device is configured to establish said second output signal indicating the state of awakening in the patient by comparing said standard deviation with a second limit value, the second signal being established as indicating awakening in the patient if the standard deviation exceeds the second limit value.

* * * * *